United States Patent [19]

Bühler et al.

[11] 4,402,685
[45] Sep. 6, 1983

[54] DIVIDABLE CATHETER

[75] Inventors: Wolfgang Bühler, Melsungen; Franz W. Brunner, Felsberg; Bodo Schacht, Malsfeld, all of Fed. Rep. of Germany

[73] Assignee: Intermedicat GmbH, Emmenbrucke, Switzerland

[21] Appl. No.: 162,621

[22] Filed: Jun. 24, 1980

[30] Foreign Application Priority Data

Jun. 30, 1979 [DE] Fed. Rep. of Germany ....... 2926572

[51] Int. Cl.³ ........................................... A61M 25/00
[52] U.S. Cl. .................... 604/280; 604/164; 525/931
[58] Field of Search ..................... 128/348, 349, 214.4, 128/DIG. 6, 221, 784; 264/173, 167; 428/23, 36; 525/931

[56] References Cited

U.S. PATENT DOCUMENTS

| T955,009 | 2/1977 | Lansbury et al. | 428/36 |
|---|---|---|---|
| 2,227,682 | 1/1941 | Wade | 264/173 |
| 3,618,614 | 11/1971 | Flynn | 128/348 |
| 3,677,243 | 7/1972 | Nerz | 128/221 |
| 3,877,429 | 4/1975 | Rasumoff | 128/221 |
| 3,963,026 | 6/1976 | Herb | 128/272 |
| 3,993,718 | 11/1976 | Bontinck et al. | 525/931 |
| 4,033,357 | 7/1977 | Helland et al. | 128/785 |
| 4,105,732 | 8/1978 | Slingluff | 264/173 |
| 4,166,469 | 9/1979 | Littleford | 128/784 |
| 4,182,582 | 1/1980 | Youval | 264/173 |
| 4,225,688 | 9/1980 | Dennehey et al. | 525/931 |
| 4,306,562 | 12/1981 | Osborne | 604/164 |

Primary Examiner—Kyle L. Howell
Assistant Examiner—Max F. Hindenburg
Attorney, Agent, or Firm—Merriam, Marshall & Bicknell

[57] ABSTRACT

A dividable short catheter tube made of a modifying polymer intermixed with, or inserted into, a base polymer. The modifying polymer is usually one which is incompatible with the base polymer.

The dividable short catheter tube is readily tearable longitudinally so that it can be removed from around a flexible catheter after the flexible catheter has been guided into a patient by means of the short catheter previously positioned in a body puncture.

The tube can be extruded from a mixture of the two polymers or it can be extruded with modifying polymer longitudinal strips in walls of the base polymer.

21 Claims, 5 Drawing Figures

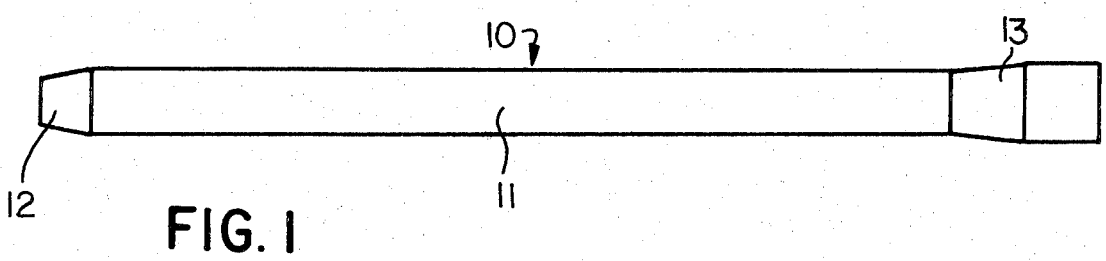
FIG. 1
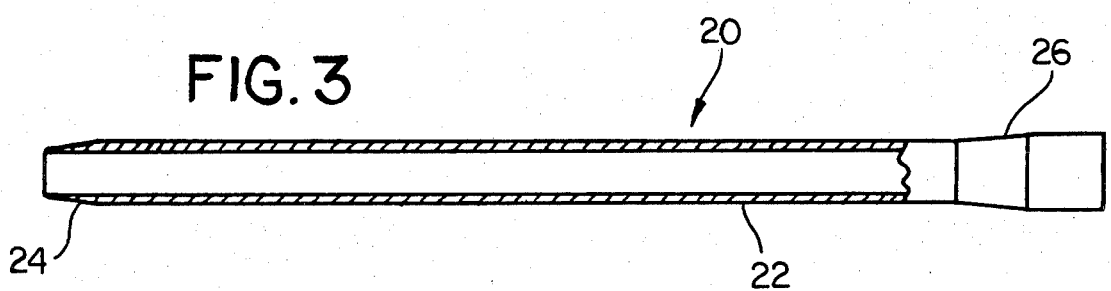
FIG. 3
FIG. 2
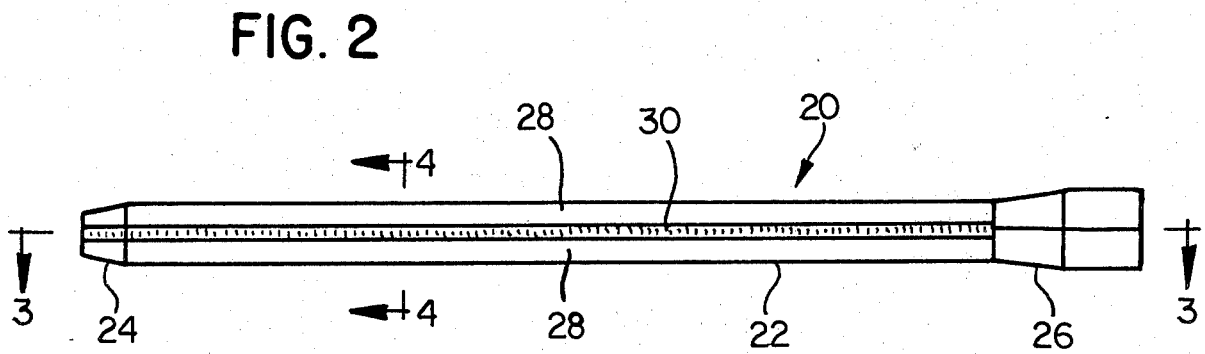
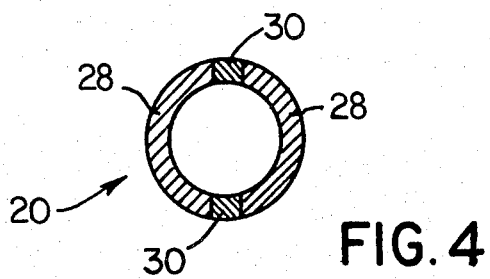
FIG. 4

DIVIDABLE CATHETER

This invention relates to catheters. More particularly, this invention is concerned with an improved short dividable catheter tube made of synthetic solid polymers.

Flexible catheters are used to conduit fluids to a patient to supply parenteral nourishment or medication. The insertion of the flexible catheter, such as into the vein of a patient, is often effected by use of an auxiliary device, one form of which is a metal tubule. After the metal tubule has made the puncture, the flexible catheter is inserted through the metal tubule into the vein.

An alternative, and safer system, is to use a short catheter made of synthetic polymeric material. This system is often used for short-term blood transfusions or for administering infusion solutions. The short catheter usually consists of a thin-walled polymeric tube having a metal puncturing tubule inside. Both of the elements have extensions, made of polymeric material, for ease of handling or for connecting with other tubes. A short catheter made of polymeric material as described, as compared to a metal tubule, is less likely to be damaged or broken off upon improper or awkward handling.

After the short catheter has been inserted, such as into a vein, the internal metal puncturing tubule is removed, leaving the end of the short catheter in place in the vein. Then, the end of a flexible catheter is inserted through the short catheter into the vein. The short catheter has an enlarged cone-shaped end to facilitate insertion of the flexible catheter. After that is done, the short catheter is withdrawn from the vein and secured to the flexible catheter outside of the patient. Usually the short catheter cannot be slid in a telescoping manner off the end of the flexible catheter because most flexible catheters have a rigid connecting attachment at the end which would prevent such removal of the short catheter.

German Pat. No. 2,104,226 discloses a device as described above for inserting a flexible catheter. The short catheter polymeric tube as therein described has longitudinal tear lines or fracture points and finger grips. When the finger grips are pulled apart, the tube can be ripped open along the tear lines and thereby removed from around the flexible catheter.

The short catheter polymeric tube is about 5 to 10 cm long so the tear lines must run the entire tube length. Obviously, the tear lines must be very exact and have a constant residual wall thickness. Producing such tear lines presents substantial problems, whether they are produced in the tube by injection molding or by machining a preformed polymeric tube having a uniform wall thickness. The initial tearing and subsequent ripping behavior over the full catheter length substantially depends on the tube residual wall thickness at the tear line. If it is made uneven or non-uniform, the tearing may terminate unintentionally before the catheter end and thus prevent division of the catheter over its entire length.

An object of the invention is to provide a short catheter tube of synthetic polymeric material which is readily dividable longitudinally by tearing but which avoids many, or all, of the shortcomings associated with previous short catheters to be torn longitudinally. A further object is to provide a dividable short catheter tube which eliminates much of the expenditure previously involved in manufacturing or machining tear lines therein.

According to the invention, short catheter tubes, readily dividable longitudinally by tearing, are provided having a composition comprising a base polymer modified by a second polymer intermixed with, or inserted into, the base polymer. Such catheter tubes can be readily and inexpensively manufactured by extrusion. Particularly useful tubes can have an outer diameter of up to 4 mm and a wall thickness of about 0.2 to 0.4 mm.

Broadly, the tube modifying polymer content can comprise about 0.5 to about 40 weight percent, and desirably about 5 to 25 weight percent, of the base polymer weight (not the weight of the mixture). The particular amount most suitable for specific polymers used, such as in a mixture of the polymers, can be easily determined by preparing compositions having different amounts of polymers.

It is generally desirable to use a base polymer which is incompatible with the modifying polymer.

Because of their chemical inertness in contact with human blood or tissue, the following mixtures of base polymer and modifying polymer are particularly useful:

| Base Polymer | Modifying Polymer |
| --- | --- |
| Polyethylene | Polypropylene |
| Polypropylene | Polyethylene |

With polypropylene as the base polymer, a suitable mixture can contain a weight ratio of about 95 to 75 weight percent of polypropylene and 5 to 25 weight percent of polyethylene having a density between 0.915 to 9.965 g/cm$^3$ as modifying polymer. When polyethylene is the base polymer and polypropylene is the modifying polymer, the ratio can also be within such amounts. Although these polymer mixtures are particularly suitable because of their chemical inertness in contact with human blood and tissue, mixtures of other base polymers and modifying polymers can be prepared which, when extruded into capillary size tubes, have the same or similar tearing and dividing properties. Representative of other polymer mixtures which can be used are:

| Base Polymer | Modifying Polymer |
| --- | --- |
| Polypropylene | Polyacrylate homo and copolymers |
| Polypropylene | Polymethacrylate homo and copolymers |
| Polypropylene | Polystyrene homo and copolymers |
| Polypropylene | Polymethylpentene-1 |
| Polypropylene | Polybutylene-1 |
| Polypropylene | Polyethylene copolymers |
| Polyethylene | Polypropylene copolymers |
| Polyethylene | Polybutylene-1 |
| Polyethylene | Polymethylpentene-1 |
| Polyethylene | Polyacrylate homo and copolymers |
| Polyethylene | Polymethacrylate homo and copolymers |
| Polyethylene | Polystyrene homo and copolymers |
| Polyvinylchloride | Polyethylene homo and copolymers |
| Polyvinylchloride | Polypropylene homo and copolymers |
| Polyvinylchloride | Polymethylpentene-1 |
| Polyvinylchloride | Polybutylene-1 |

The invention will be described further in conjunction with the attached drawings, in which:

FIG. 1 shows a short catheter tube formed by extrusion of a mixture of base polymer and modifying polymer;

FIG. 2 shows another embodiment of short catheter provided by the invention;

FIG. 3 is a sectional view taken along the line 3—3 of FIG. 2;

FIG. 4 is a sectional view taken along the line 4—4 of FIG. 3; and

Figure 5:
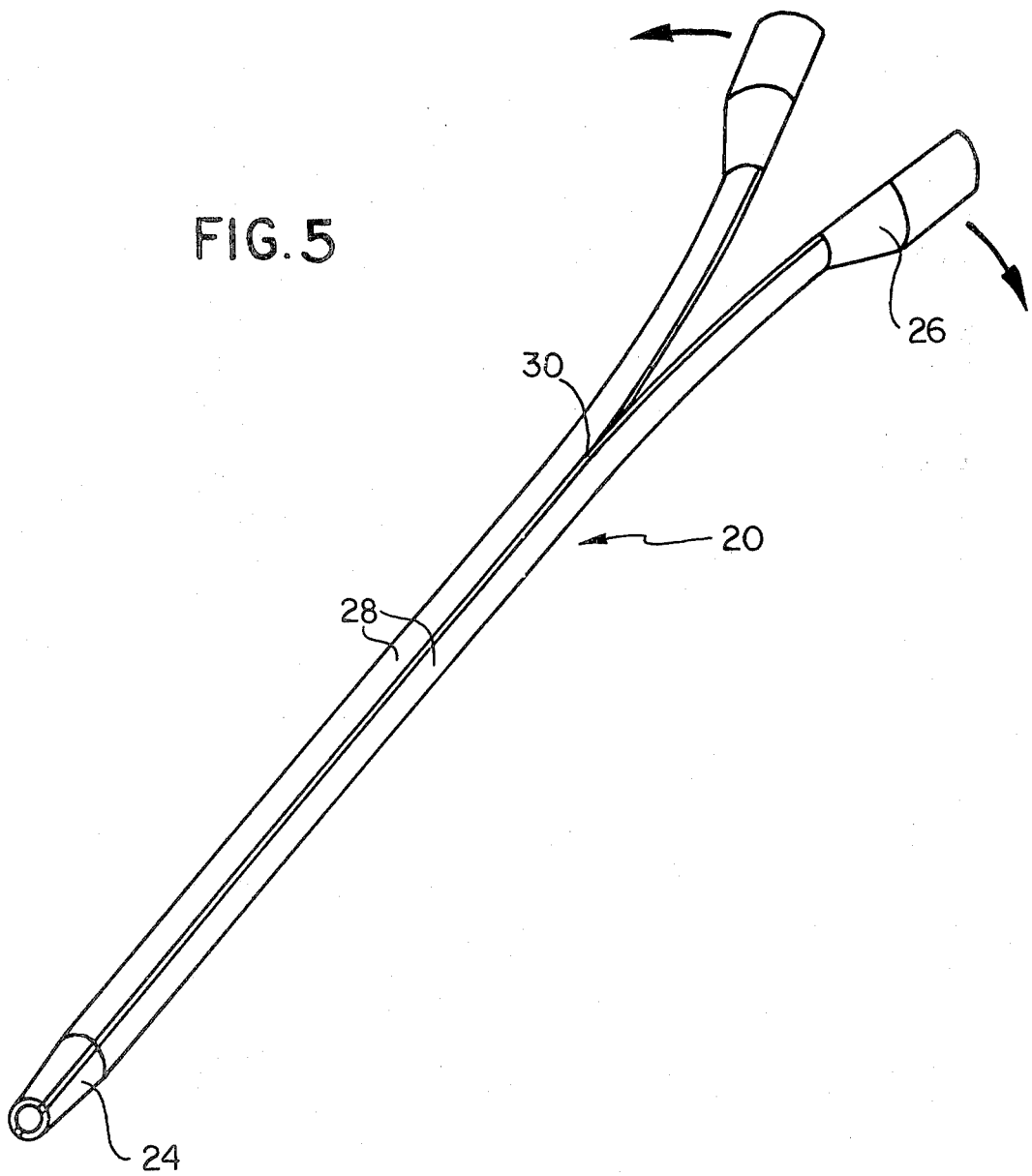
FIG. 5 is an isometric view of the catheter, shown in FIGS. 2 to 4, being torn longitudinally and thereby divided.

The short catheter 10 shown in FIG. 1 has a tubular body 11 with a tapered front end 12 and enlarged conical back end 13. It has a longitudinal axial hole which is not shown but which is sized to receive a metal puncturing tubule. The short catheter 10 is readily formed by first extruding a mixture of a base polymer and a modifying polymer to form tube 11. Tapered front end 12 can then be formed and enlarged conical end 13 added. Any suitable mixture of base polymer and modifying polymer described above can be used to make the short catheter.

FIGS. 2 to 4 illustrate a second embodiment of dividable short catheter provided by the invention. The short catheter 20 has a tubular body 22, a tapered front end 24 and an enlarged conical attachment end 26. The catheter tubular body 22 is formed by simultaneously extruding a base polymer to form the two semicircular walls 28 which are joined to two strips 30 of simultaneously extruding modifying polymer. The two strips 30 are located 180° apart. They can be made about 0.3 to 1.0 mm wide.

FIG. 5 illustrates the short catheter of FIGS. 2 to 4 being divided by the application of lateral tensile force in the direction of the arrows. The short catheter is thereby readily torn longitudinally along the two strips 30 which are not fused strongly to the walls 28 because of the incompatibility of the two polymers.

The following examples are presented to further illustrate the invention.

EXAMPLE 1

Eighty parts by weight of polypropylene homopolymer in granular form having a density of 0.902 g/cm$^3$ and a melting index MFI 230/5 of 7 g/10 min., and 20 parts by weight of a polyethylene homopolymer in granular form having a density of 0.920 g/cm$^3$ and a melting index of MFI 190/2 of 6 g/10 min. are thoroughly mixed and melted in a screw extruder, extruded as a strand and then crushed in a granulator to small cylindrical granules.

From the granulate, a capillary tube having a 1.5 mm ID (inner diameter) and 2.0 OD (outer diameter) is extruded from the granules. A section of tube about 5 cm long is connected at one end to a catheter attachment having finger grips for longitudinally dividing it. The tensile strength of the tube-attachment connection, in the longitudinal direction, is at least 20 N. A puncturing metal tubule with tubule attachment is then inserted in the short catheter.

If the complete puncturing device is used as an auxiliary device for inserting a flexible catheter into the vein of a patient to be treated, the vein is punctured, the metal tubule is removed and a suitable flexible catheter is pushed forward through the short catheter left in place. As soon as the flexible catheter has been inserted, the short catheter surrounding the flexible catheter is slid back and removed. To remove the short catheter, the grips provided at the short catheter attachment are fitted between the thumb and the forefinger of each hand and pulled laterally thus tearing the tube lengthwise by further lateral pulling. The grips and the longitudinally severed tube can be completely removed from the flexible catheter in this way.

EXAMPLE 2

Ninety parts by weight of a polyethylene homopolymer in granular form having a density of 0.960 g/cm$^3$ and a melting index of MFI 190/2 of 5 g/10 min., and 10 parts by weight of a polypropylene copolymer (copolymer with 2% ethylene as a co-monomer) having a density of 0.905 g/cm$^3$ and a melting index of MFI 230/5 of 3.5 g/10 min., are mixed and melted in a screw extruder, extruded as a strand, and the strand then crushed in a granulator to cylinder granules.

A short catheter capillary tube having a 1.0 mm ID (inner diameter) and 1.45 mm OD (outer diameter) is extruded from the granules. A 4 cm long section of the tube is fitted at one end with an attachment having grips for longitudinally dividing the catheter by pulling it laterally and tearing it. The tensile strength of the tube-attachment connection in the longitudinal direction is at least 15 N without separation of the connection. The tube can be fitted with a metal puncturing tubule as described in Example 1 and it can be used as described in that example.

The foregoing detailed description has been given for clearness of understanding only, and no unnecessary limitations should be understood therefrom, as modifications will be obvious to those skilled in the art.

What is claimed is:

1. A short catheter tube dividable longitudinally be tearing comprising a tube wall made of modifying polymer intermixed with a base polymer incompatible with the modifying polymer, with both the base polymer and the modifying polymer being inert to human blood and tissue.

2. A dividable short catheter according to claim 1 in which the base polymer is polypropylene and the modifying polymer is a (1) polyacrylate homo or copolymer, (2) polymethacrylate homo or copolymer, (3) polystyrene homo or copolymer, (4) polymethypentene-1, (5) polybutylene-1, or (6) polyethylene copolymer.

3. A dividable short catheter according to claim 1 in which the base polymer is polyethylene and the modifying polymer is a (1) polypropylene copolymer (2) polybutylene-1, (3) polymethylpentene-1, (4) polyacrylate homo or copolymer, (5) polymethacrylate homo or copolymer, or (6) polystyrene homo or copolymer.

4. A dividable short catheter according to claim 1 in which the base polymer is polyvinylchloride and the modifying polymer is a (1) polyethylene homo or copolymer, (2) polypropylene homo or copolymer, (3) polymethylpentene-1, or (4) polybutylene-1.

5. A dividable short catheter tube according to claim 1 in which the amount of modifying polymer is about 0.5 to 40 weight percent of the base polymer.

6. A dividable short catheter tube according to claim 1 in which the amount of modifying polymer is about 5 to 25 weight percent of the base polymer.

7. A dividable short catheter tube according to claim 1 in which the base polymer is polypropylene and the modifying polymer is polyethylene.

8. A dividable short catheter tube according to claim 1 in which the base polymer is polyethylene and the modifying polymer is polypropylene.

9. A dividable short catheter tube according to claim 1 in which the tube is an extruded mixture of the base polymer and the modifying polymer.

10. A dividable short catheter tube according to claim 1 in which the tube is an extruded mixture and the amount of modifying polymer is about 0.5 to 40 weight percent of the base polymer.

11. A dividable short catheter tube according to claim 1 in which the tube is an extruded mixture and the amount of modifying polymer is about 5 to 25 weight percent of the base polymer.

12. A short catheter tube dividable longitudinally by tearing comprising a tube wall made of a base polymer and having at least two longitudinal strips of modifying polymer that extend the length thereof, wherein said base polymer and said modifying polymer are incompatible and inert to human blood and tissue whereby said catheter tube is dividable along said longitudinal strips.

13. A dividable short catheter according to claim 12 in which the base polymer is polypropylene and the modifying polymer is a (1) polyacrylate homo or copolymer, (2) polymethacrylate homo or copolymer, (3) polystyrene homo or copolymer, (4) polymethylpentene-1, (5) polybutylene-1, or (6) polyethylene copolymer.

14. A dividable short catheter according to claim 12 in which the base polymer is polyethylene and the modifying polymer is a (1) polypropylene copolymer (2) polybutylene-1, (3) polymethylpentene-1, (4) polyacrylate homo or copolymer, (5) polymethacrylate homo or copolymer, or (6) polystyrene homo or copolymer.

15. A dividable short catheter according to claim 12 in which the base polymer is polyvinylchloride and the modifying polymer is a (1) polyethylene homo or copolymer, (2) polypropylene homo or copolymer, (3) polymethylpentene-1, or (4) polybutylene-1.

16. A dividable short catheter tube according to claim 12 in which the amount of modifying polymer is about 0.5 to 40 weight percent of the base polymer.

17. A dividable short catheter tube according to claim 12 in which the amount of modifying polymer is about 5 to 25 weight percent of the base polymer.

18. A dividable short catheter tube according to claim 12 in which the base polymer is polypropylene and the modifying polymer is polyethylene.

19. A dividable short catheter tube according to claim 12 in which the base polymer is polyethylene and the modifying polymer is polypropylene.

20. A dividable short catheter tube according to claim 12 in which the tube is an extruded mixture of the base polymer and the modifying polymer.

21. A dividable short catheter tube according to claim 12 in which the tube wall comprises the base polymer and the tube wall contains only two longitudinal strips of modifying polymer offset 180°.

* * * * *